United States Patent [19]

Shaffer

[11] 3,982,531
[45] Sept. 28, 1976

[54] INFLATION DEVICE FOR A PNEUMATIC ORTHOSIS

[75] Inventor: Donald E. Shaffer, Newark, Del.

[73] Assignee: Thiokol Corporation, Newtown, Pa.

[22] Filed: Apr. 30, 1975

[21] Appl. No.: 572,980

[52] U.S. Cl.................................. 128/24 R; 128/64; 128/DIG. 20; 135/65
[51] Int. Cl.².......................................... A61H 1/00
[58] Field of Search............... 135/47; 128/DIG. 20, 128/25 R, 87 R, 24 R, 64; 9/321, 328; 42/1 G, 52; 222/78

[56] References Cited
UNITED STATES PATENTS

| | | | |
|---|---|---|---|
| 1,598,784 | 9/1926 | Rae et al.............................. | 42/1 G |
| 2,699,165 | 1/1955 | Ferrier.......................... | 128/DIG. 20 |
| 3,823,711 | 7/1974 | Hatton............................. | 128/78 |
| 3,823,712 | 7/1974 | Morel........................... | 128/DIG. 20 |
| 3,833,029 | 9/1974 | Munn.................................. | 9/321 |
| 3,868,952 | 3/1975 | Hatton........................ | 128/DIG. 20 |
| 3,877,882 | 4/1975 | Lette et al.............................. | 9/321 |

FOREIGN PATENTS OR APPLICATIONS

| | | | |
|---|---|---|---|
| 1,472,902 | 2/1967 | France..................................... | 9/321 |
| 62,043 | 10/1912 | Sweden................................. | 135/47 |
| 388,092 | 2/1933 | United Kingdom..................... | 9/321 |

*Primary Examiner*—Werner H. Schroeder
*Assistant Examiner*—Conrad L. Berman
*Attorney, Agent, or Firm*—Stanley A. Marcus; William R. Wright, Jr.

[57] ABSTRACT

A gas generating inflation device utilizing combustible propellant cartridges is provided for a pneumatic orthosis used by persons needing support of the legs or lower body and legs. Since most such persons use two canes for additional support while standing or walking, the inflation device is conveniently located in one of the canes, with the other cane used as a supply container for additional cartridges. The gas generator is loaded with a propellant cartridge and gas generation is initiated at the will of the orthosis wearer, the generated gas then flowing through filters in the cane in which the generator is located and thence into the pneumatic orthosis to inflate it.

14 Claims, 10 Drawing Figures

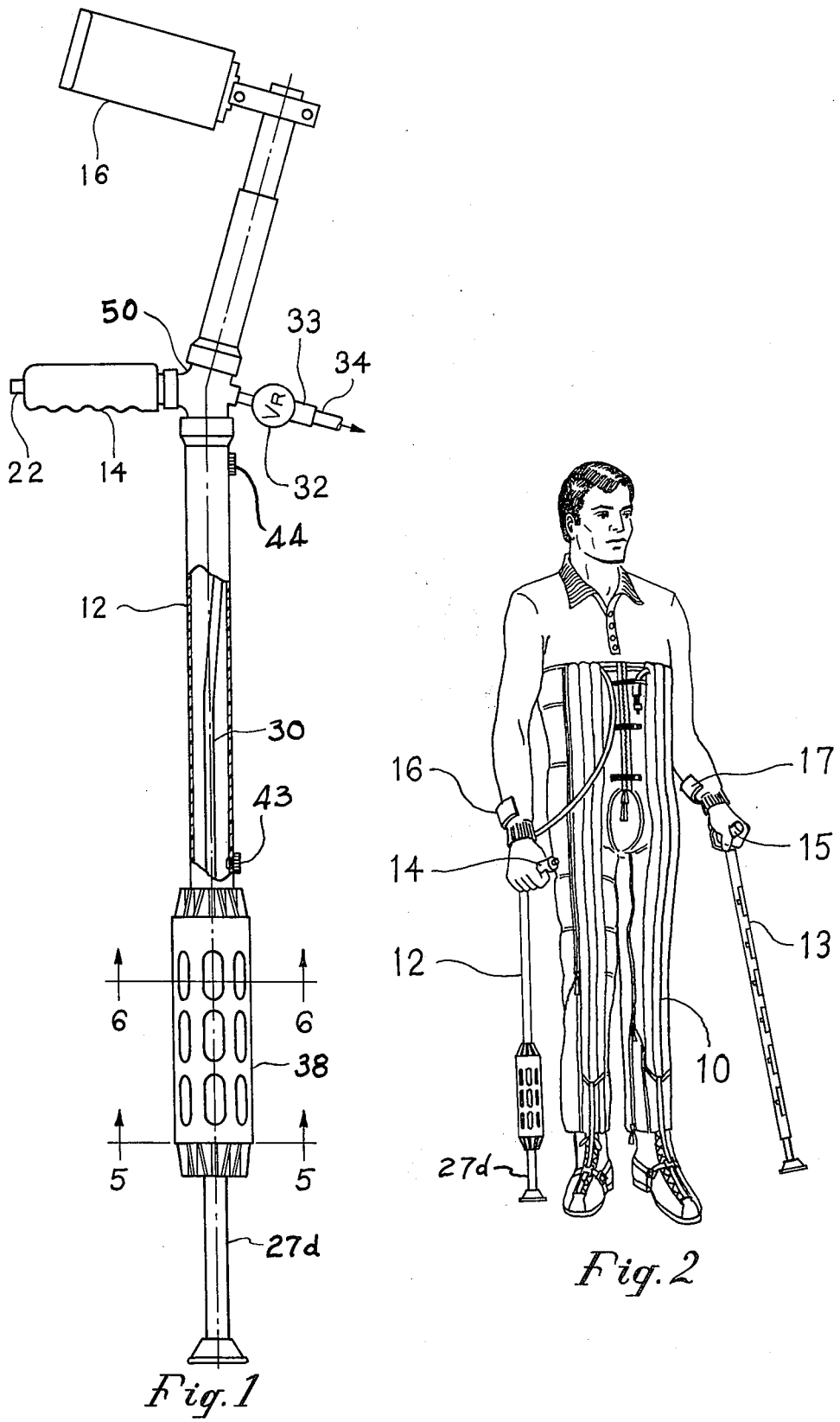

INFLATION DEVICE FOR A PNEUMATIC ORTHOSIS

BACKGROUND OF THE INVENTION AND DISCUSSION OF THE PRIOR ART

A recent concept in the art of bracing for paraplegic and hemiplegic persons is that of pneumatic orthoses such as are described in U.S. Pat. Nos. 3,823,711, 3,823,712 and 3,868,952. These are essentially lightweight fabric garments with integral pneumatic closed beams which when inflated with a gas under pressure form a rigid exo-skeleton covering the wearer's legs or body from the chest down as well as the legs which provides the needed support. The garment is usually worn over underwear but is covered by outer wear.

When the wearer wishes to sit, the pneumatic orthosis must be deflated by allowing gas to escape through a valve which the wearer operates. This allows the pneumatic beams to collapse and allows for the free knee and hip movement necessary to achieve a sitting position. However, when a standing position is again assumed, it is necessary that the pneumatic orthosis be re-inflated and this inflation has been accomplished up until now by the use of a pressurized gas bottle or an air pump which, although they do inflate the orthosis, tend to be somewhat slow in operation, are quite heavy and cumbersome and involve extra equipment which constitute a considerable bother and exertion to the wearer.

The present invention, however, provides the wearer with an inflation device which generates inflating gas rather than stores it and which is almost completely housed in the crutch-like cane or canes which a person would normally be using anyway if he were in need of the orthosis. Such an arrangement represents a considerable improvement over the pressure bottles or air pumps since no such cumbersome, bothersome or heavy extra or loose equipment is needed and yet the inflation can be expected to be positive, rapid and effective. The convenience and lightweight to a person needing an orthosis is believed to be great and a very important factor in avoiding both fatigue and frustration and thus permitting the person to accomplish much more during his day's activities than might otherwise be the case.

OBJECTS OF THE INVENTION

It is, therefore, an object of the present invention to provide a gas generator inflator for producing gas under pressure for the inflation of a pneumatic orthosis.

It is also an object of the present invention to provide a gas generator of the foregoing type wherein the produced gas is cooled, filtered and dried sufficiently so that it should not be harmful to a person nor to the pneumatic orthosis during normal operation.

It is also an object of the present invention to provide a gas generator of the foregoing type wherein the generator is housed in at least one of the canes normally used by a pneumatic orthosis wearer in order to eliminate the carrying of cumbersome and heavy extra or loose equipment.

It is also an object of the present invention to provide a pneumatic orthosis inflation device wherein pressurizing propellant charges may be quickly and easily loaded and reloaded allowing any number of inflations per day which has not been altogether practical with other systems.

It is also an object of the present invention to provide a pneumatic orthosis inflator of the foregoing type wherein the propellant and igniter element are included in an easily replaceable cartridge.

It is also an object of the present invention to provide a replaceable cartridge as set forth in the previous paragraph but including a built in filter.

It is also an object of the present invention to provide a pneumatic orthosis inflator of the foregoing type wherein the gas generated by the gas generator is filtered, substantially neutralized and substantially dried before its entry into the pneumatic orthosis.

It is also an object of the present invention to provide a pneumatic orthosis of the foregoing type wherein the gas generator, filter, neutralizer and water removal means are all housed in an invalid's cane.

It is also an object of the present invention to provide for storage of additional gas generator cartridges in a second invalid's cane.

Other objects and advantages of the present invention will become apparent from the detailed description and claims which follow.

In the drawings:

FIG. 1 is an overall longitudinal partially cross-sectional view of the whole gas generator and cane;

FIG. 2 is a view of a pneumatic orthosis worn by a person and showing the use of the canes;

DETAILED DESCRIPTION OF THE INVENTION

Figure 3:
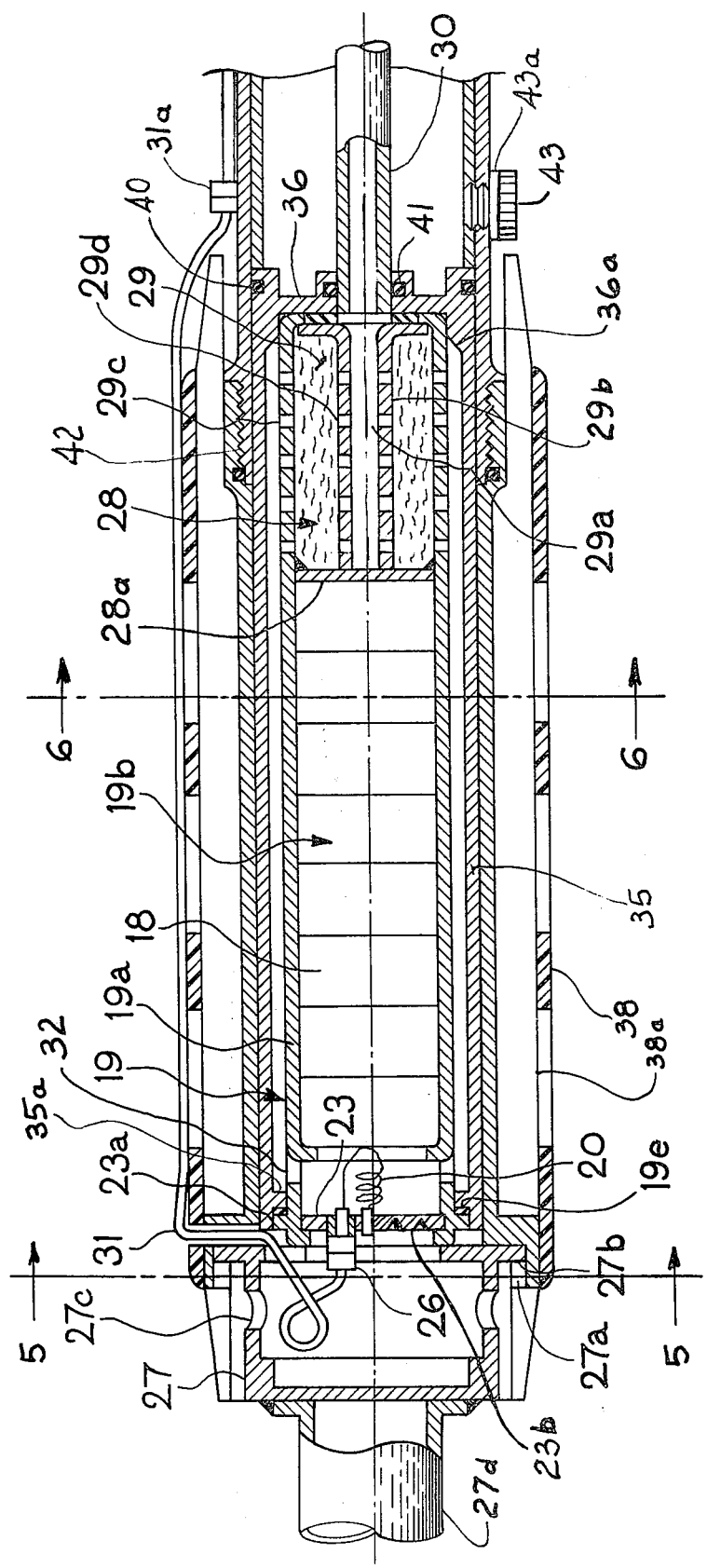
FIG. 3 is a longitudinal partially cross-sectional view of the lower end portion of the cane showing the combustion chamber and the propellant and filter cartridge.

With reference to FIG. 2, a pneumatic orthosis or supporting garment 10 having pneumatic beams is shown worn by a person having a paraplegic or hemiplegic problem and who therefore needs the support in order to become mobile. Also, the person is shown with two supporting crutches or invalid's canes 12, 13 which the person uses by grasping handles 14, 15, respectively, and allowing arm partially encircling clamps 16, 17 to lend support to the upper arm. It will be seen that when the pneumatic beams are inflated sufficiently to become stiff, the portion of the person's body which is covered by the orthosis is supported strongly and dependably. On the other hand, in order for the person to sit down, the pneumatic beams of the orthosis must be deflated in order to allow them to bend, thus necessitating their re-inflation in order to make the orthosis in condition to again give support. The gas for each inflation cycle is provided by a propellant 18 located in a combustion chamber 19b in propellant cartridge 19 in the lower end of first cane 12. This is a combustible solid propellant and is ignited in this embodiment by contact with an electrically heated "hot" wire igniter 20, the electricity to heat the wire supplied by a small dry battery or batteries 21, 21a preferably of the rechargeable type and located either in the handle as in the case of battery 21 or in the foot of cane 12 as in the case of battery 21a shown in FIGS. 4 and 7 respectively and connected through a switch 22 (FIG. 1) located on the handle 14 where the user can reach it easily. The batteries are grounded on their bottoms by flat springs 21b or 21c attached to the cane 12. Propellant cartridge 19 includes an outer wall 19a defining and enclosing a combustion chamber 19b, and a filter chamber 28 separated by solid wall 28a and closed at its left end in FIGS. 3 and 7 by end wall 23 permanently held in place by a rolled edge as shown and an annular projection 23a integral with the outer wall 19a is provided as shown. End wall 23 includes a purposely weakened portion or "disk" 23b defined by an annular V cut in the surface of end wall 23 as shown to form a weakened section and also to concentrate stresses at the apex of the V. The V cut is deep enough to insure a failure in shear at that annular line in the event of excessive pressure in the combustion chamber 19b with a consequent blow-out of the disk 23b and relief of the pressure as described later in this specification. In the outer wall 19a are open ports 32 having a portion of their edge walls bent inward in the manner of tabs to serve as retainers for propellant 18 so as to prevent the propellant from blocking ports 32.

Figure 4:
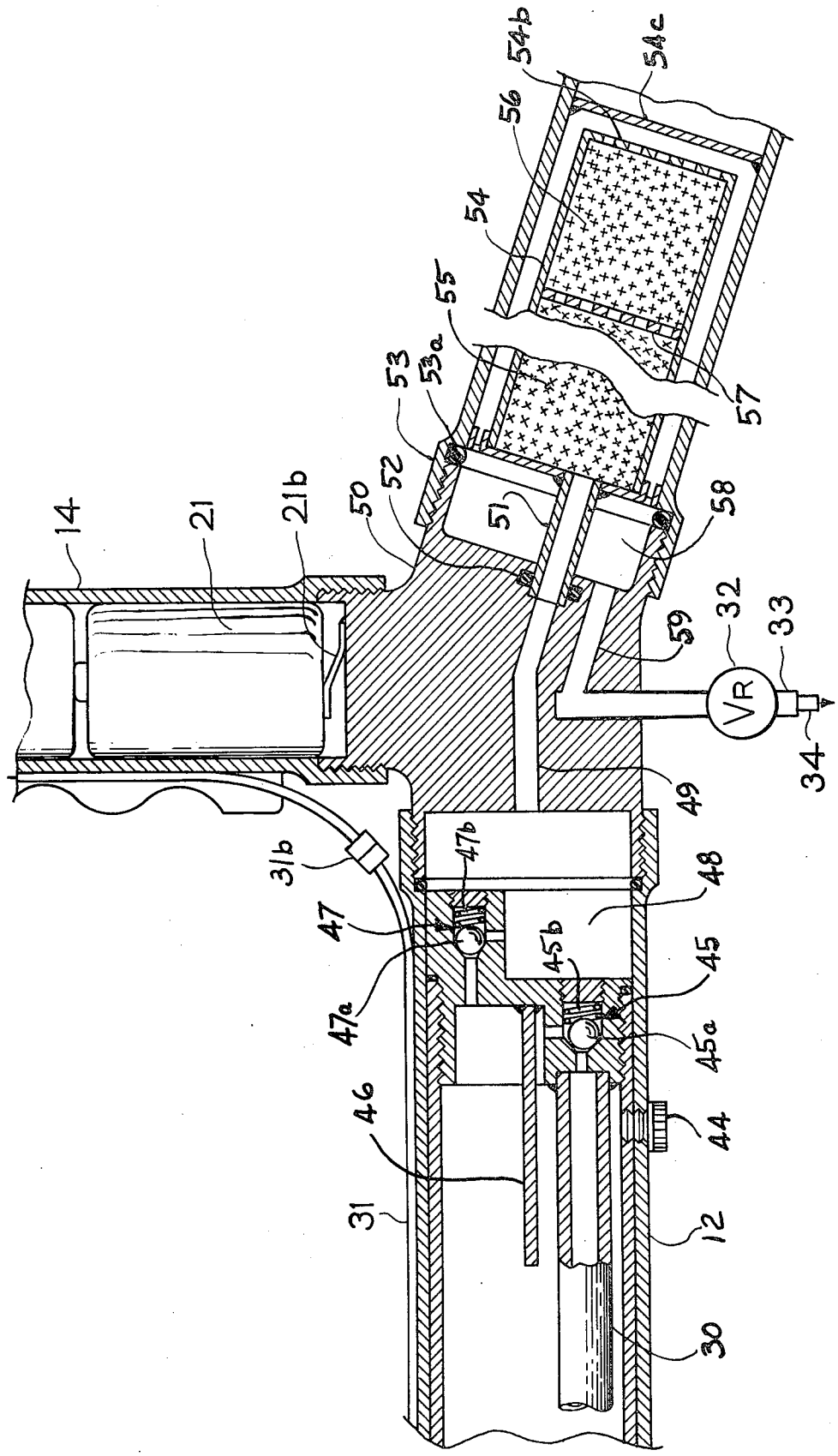
FIG. 4 is a longitudinal cross-sectional view of the handle area of the cane showing the water trap, neutralizer, dessicator and battery.
Figure 7:
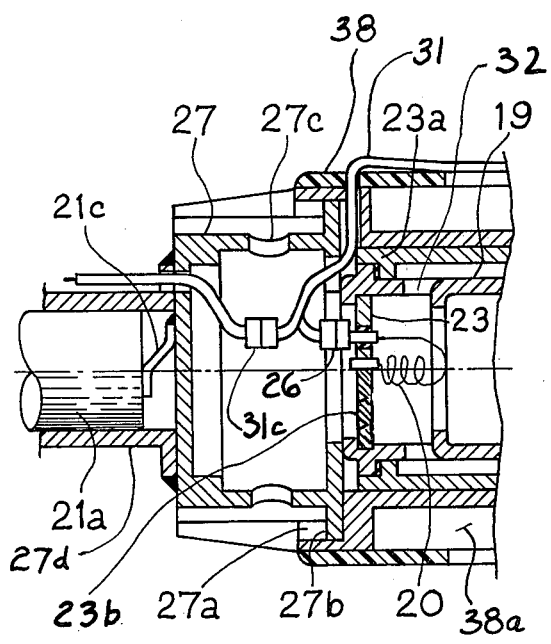
FIG. 7 is a partially longitudinal cross-sectional view of the lower end of the combustion chamber and foot area showing the battery located in the foot.

As mentioned in the foregoing paragraph, combustion chamber 19b at end wall 23 includes igniter "hot" wire 20 which is grounded to end wall 23 and thus to the structure of cane 12 at one end, curls into chamber 19b to contact solid propellant 18, also contained in chamber 19b as shown and then passes through end wall 23 in electrically insulated relationship thereto to connector plug 26 itself electrically connected to wire 31. Wire 31 includes plug-in connectors 31a, 31b adjacent to the screw joints in the cane 12 as shown in FIGS. 3 and 4 so that the parts of the cane can be disassembled if required for cleaning, refurbishing or replacement. Additional plug-in connector 31c is provided adjacent to cap 27 as shown in FIGS. 3 and 7.

With reference to FIG. 3, the right hand end of wall 19a, as mentioned previously, encloses an annular filter chamber 28 containing a filter 29 and having a central open passage 29a defined by tube 29b, the right hand end of which is flared outwardly to form an end closure for chamber 28 as shown and with the end of wall 19a crimped over to hold it in place. Communication with chamber 28 is provided through open ports 29c through wall 19a and open ports 29d through the wall of tube 29b.

Figure 5:
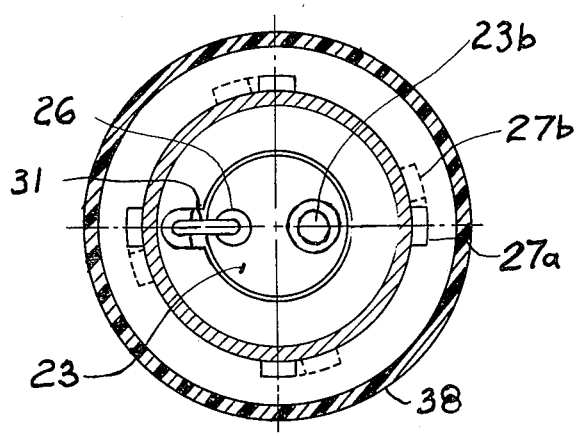
FIG. 5 is a transverse cross-sectional view taken on line 5—5 looking upwardly of the cane.
Figure 6:
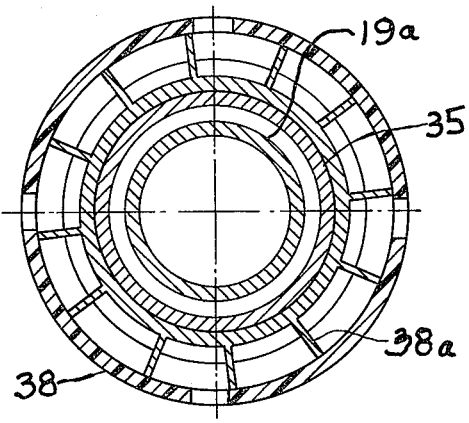
FIG. 6 is a transverse cross-section of the combustion chamber area of the cane taken on line 6—6 looking upwardly of the cane.

At the lower end of the gas generator just described, cap 27 is fitted in place by aligning tabs 27b on its exterior rim into slots 27a as shown in FIGS. 3 and 5 which are elongated as shown dotted in FIG. 5 so that after the tabs have been placed in the slots (i.e. a bayonet type connection) cap 27 can be rotated until it is locked in place longitudinally and can be removed only by reversing the rotation until the slots are re-aligned. Open ports 27c are provided in the side walls of cap 27 for purposes to be explained later in this specification and attached to cap 27, or made integral with it, is foot 27d which extends downward from it to the ground and has a resilient cover on its lower end to serve as a non-skid means.

As can be seen from the foregoing description, the propellant cartridge and filter chamber 28 form a unitary structure separate from the rest of the cane 12 and therefore represent an easily insertable, removable and replaceable part. The propellant 18 is preferably formed into a cylindrical shape and is put into place in the combustion chamber 19b as shown leaving space at the lower end for the igniter element, this being done at the factory with the user receiving the complete cartridge 19.

An outer jacket 35 is provided about cartridge 19 and is of larger diameter so that an annular space is provided between the jacket and chamber 19 to provide a passage through which gas may pass and cartridge 19 has gas exit ports 32 located in its wall as shown which afford communication between the interior of cartridge 19 and the space between its wall and jacket 35. An annular lip 35a is provided on the inner surface of jacket 35 at its lower end (at the left in FIG. 3) which is fitted with a gasket 19e on its lower side adapted to bear upon lip 23a on cartridge 19 in gas sealing relationship thereto while at the opposite or upper end of jacket 35 is wall 36 which has an internal annular shoulder 36a adapted to receive the end of cartridge 19 and to position it axially of cane 19 as shown in FIG. 3. The shoulder 36a is bevelled as shown to aid the insertion of cartridge 19. As will be seen from FIG 3, a gas-tight gasket seal 27 is included between cartridge 19 and wall 36 and it is attached to cartridge 19 adhesively or by other means (not shown) so that it will be in its proper position as cartridge 19 is installed. The outer wall of jacket 35 includes an O-ring seal 40 which precludes gas from escaping past this location. Also, a heat protective shield or shroud 38 of phenolic or plastic material is provided about heat dissipation fins 38a with openings in it to provide air circulation.

Wall 36 includes a central hole and O-ring seal 41 into which a hollow tube 30 extends as shown in FIG. 3 with a slide fit in gas-sealing relationship thereto. This is made so as to be demountable in order that the lower portion of the cane 12 may be removed if necessary for any reason which is accomplished by unscrewing of the threads 42. Also, a drain plug 43 is located in the wall of cane 12 close to wall 36. Plug 43 includes a sealing gasket 43a and is threaded through the wall of cane 12 to prevent leakage of gas or water as will be explained later in this specification. Another similar plug 44 is provided in the wall of cane 12 higher up the cane as shown in FIGS. 1 and 4, the purpose of which will also be explained later in this specification. Tube 30 passes upwardly from wall 36 through the hollow shaft of the cane to spring-loaded inlet check valve 45 which is normally closed until gas pressure is applied to it through the tube 30. This check valve includes a right angle passage and a spring-loaded ball 45a adapted to close it normally until such time as gas pressure entering from tube 30 pushes the ball off its seat. The right angle passage communicates from tube 30 with the hollow interior of the cane 12 and is directed toward a baffle plate 46 adjacent to it. Another similar outlet check valve 47 is included which acts as an exit valve from the interior of the cane and it too is normally closed by the biasing action of its spring acting upon its ball 47a to urge it to its seat. The hollow interior and the baffle and check valve system form an area which can be called a water trap or collector with the drain plug 43 included at its lower end to provide drainage when needed and plug 44 at its upper end to allow for flushing. Outlet check valve 47 opens into a chamber 48 in communication with a passage 49 in handle junction member 50 with passage 49 in communication with pipe 51. An O-ring seal 52 is provided at this point to effect a gas-tight seal since the pipe 51 is slid out of place in member 50 should the upper portion of the cane be disassembled by unscrewing it at threads 53. A gasket or O-ring seal 53a is provided at the threaded portion as shown and reassembly is accomplished by re-screwing the threaded portion onto member 50.

As will be seen in FIG. 4, pipe 51 communicably leads into the interior of replaceable canister 54 entering first into neutralizer chamber 55 which in turn communicates with dessicant chamber 56, the two chambers being separated by perforated separator plate or screen 57 in the manner shown. The canister 54 has a perforated end wall 54b to afford communication with a space between canister 54 and the exterior wall of cane 12 and thus to communicate with the collection chamber 58. A passage 59 in member 50 communicates with chamber 58 and with pressure regulator 32 which, in turn, communicates with quick-disconnect connector 33 and thence with the hose 34 leading to the pneumatic orthosis.

The material used in the filter 29 is preferably activated charcoal or the like but other materials can be used if they are capable of filtering out particles of propellant, will stay in place and be relatively inert chemically and substantially unaffected by the heat of the gases. The neutralizer is preferably sodium bicaronate while the dessicant is preferably a molecular sieve.

The solid propellant 18 can be in a number of forms such as a single cartridge or several pellets which will fit and will be properly retained in position in combustion chamber cartridge 19. Various formulations of propellant could be used if they have the necessary qualities of substantial non-toxicity, substantial non-corrosivity and relatively acceptable low temperature of combustion. Among those which are believed to be satisfactory are dihydroxygloxime formulations such as are described in U.S. Pat. No. 3,362,859 to Sutton et al, and used in a quantity of about 0.1 lbs. to about 0.12 lbs.

Figure 10:
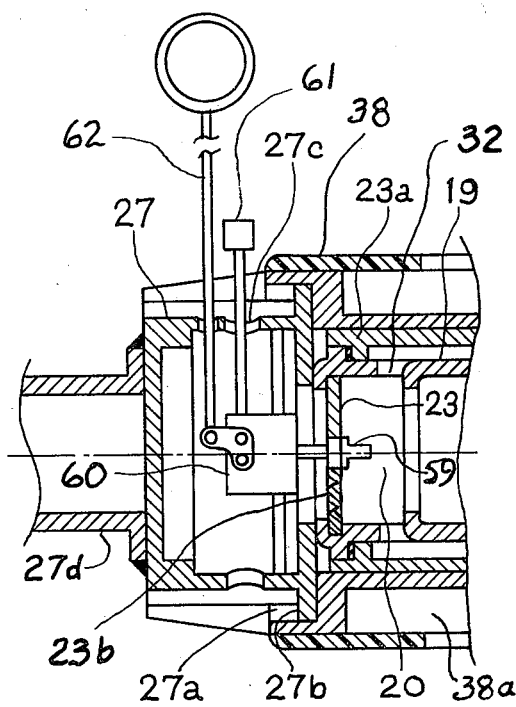
FIG. 10 is a partially longitudinal cross-sectional view of the lower end of the combustion chamber and foot area showing a percussion ignition system.

While an electrical ignition system has been described herein, a percussion type of system could also be used such as is shown in FIG. 10. This system includes a percussion cap or ignition initiator 59 in end wall 23 of cartridge 19, a trigger mechanism 60, a pull pin 61 which cocks the trigger mechanism and a lanyard 62 for pulling the trigger to release the cocked trigger mechansim and allow it to strike upon the percussion cap 59 to cause it to ignite. Upon its ignition, its generated heat ignites propellant 18 which burns and generates gas in the same manner as discussed in the foregoing paragraphs. In this embodiment the percussion cap 59 is built in end wall 23 and goes with the cartridge unit 19 so that replacement of the cartridge also provides a new percussion cap in a "ready to use" condition.

OPERATION OF THE INVENTION

When the person wearing the pneumatic orthosis decides that it should be inflated, he first removes foot cap 27 by rotating it sufficiently to line up the ears 27b with the slotted openings 27a and then pulls it free after which he unplugs wire 31. A propellant cartridge 19 is then slid into place into jacket 35 as far as it will go, the wire 31 is plugged in and cap 27 is replaced in reverse manner to the way it was removed. He then connects hose 34 to the cane gas outlet "quick disconnect" connector 33 and checks to see that it is communicably connected to the pneumatic orthosis. When these things have been accomplished, inflation is initiated by depression of the starting or ignition switch 22 which completes an electrical circuit from the live side of battery 21 through wire 31 to igniter "hot" wire 20 and to ground (the cane structure) and thus causes propellant 18 to become heated and ignited. As combustion takes place, gases are generated rapidly and pass out of cartridge 19 through ports 27c into the space between the wall of cartridge 19 and its jacket 35 and enter filter chamber 28 and filter 29 through ports 29c. Although it is most unlikely that pressure should ever become excessively great in cartridge 19, if it should, the weakened portion or "disk" 23b of end wall 23 would blow out allowing gas to enter cap 27 and to pass out into the atmosphere through ports 27c and thus relieve the internal pressure.

In the event that a percussion ignition system is used instead of the electrical system, the foot cap 27 is again removed in the same manner, except that there is no wire to unplug. A fresh cartridge 19 is slid all the way into place in jacket 35 and cap 27 is replaced as before but with no wire to plug in after which the user connects hose 34 as before and is ready to start the inflation by initiating combustion. He first cocks the trigger mechanism by pulling pin 61 and then pulls lanyard 62 to trip the trigger and cause a hammer (not shown) to strike upon percussion cap 59 to fire it. The propellant 18 then becomes ignited and gas is generated by the combustion.

After the gas from the combustion chamber 19 has entered chamber 28, it passes through filter 29, being filtered of objectionable particles as it does so, and through ports 29d enters tube 29a passing through it into tube 30 and thus reaches check valve 45. The ball 45a of this valve is then pushed off its seat by the pressure of the gas overcoming the spring 45b and gas flows out of its right angle passage striking against baffle plate 46 and passing around it to fill the interior of the cane 12 and to pressurize it. As the gas strikes the relatively cold interior wall of the cane, water vapor produced by the combustion process is condensed and runs down the interior of the wall to collect at the lower end being retained there by the closed bottom of jacket 35. The foregoing structure is termed a water trap, and, it is anticipated that a considerable number of cycles of operation can be accomplished without the necessity of draining. Drain plug 43 can be removed so that water can be drained occasionally by simple removal of the plug but it must be replaced prior to another use of the apparatus. Plug 44 can also be removed so that the trap can be flushed out if desired and it too must be replaced prior to use of the aparatus.

The pressurized and relatively dry gas thus reaches check valve 47 which opens in the same manner as the first check valve upon the urging of ball 47a against its spring 47b and allows gas to flow through its right angled passage into chamber 48 and into passage 49 in handle junction member 50. The gas then passes through pipe 51 into canister 54 where it enters a neutralizer 55 and passes therethrough, through perforated separator plate 57 into and through dessicant 56 where substantially all of the last traces of moisture are removed from it, and out of canister 54 through perforated end wall 54b. The gas is prevented from flowing up the cane by wall 54c and instead flows around canister 54 and into chamber 58 and through passage 59 into pressure regulator 32 where its pressure is automatically controlled to the proper inflation pressure after which it passes through connector 33 into hose 34 and thence enters the pneumatic beams of the pneumatic orthosis to inflate and pressurize them. An atmospheric vent valve (not shown) is included with the pneumatic orthosis garment itself for use when the user decides to deflate the garment when, for instance, he wishes to sit. This valve is usually of a type which closes automatically after deflation has occurred and thus is closed before re-inflation is commenced. Re-inflation is again accomplished, when desired, by the insertion of a new propellant cartridge and a repetition of the inflation cycle and this can be repeated as many times as desired during a single day.

Figures 8, 9:
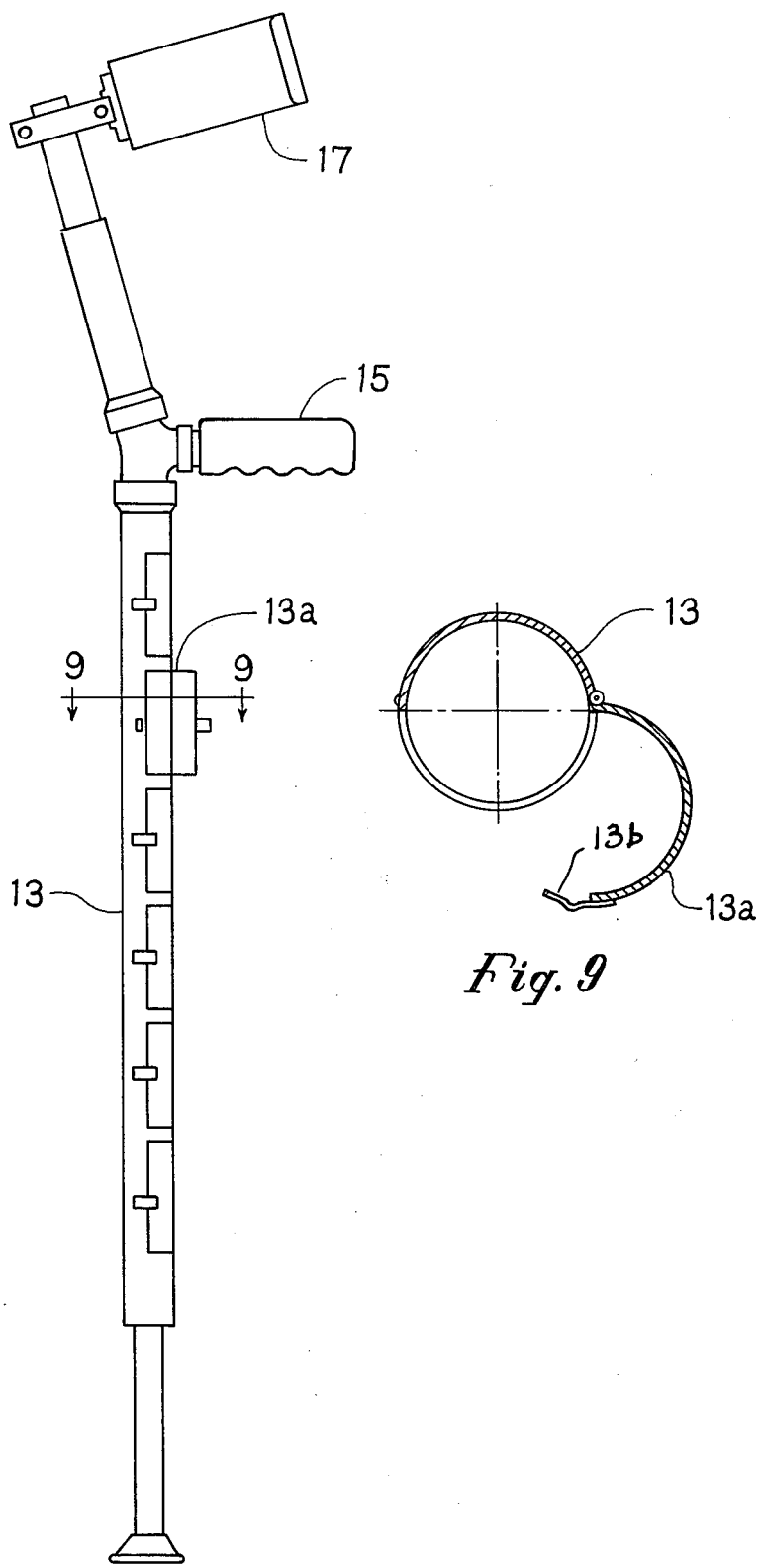
FIG. 8 is an external view of the second cane showing the access doors to the propellant storage compartments in its leg.
FIG. 9 is a transverse cross-sectional view taken on line 9—9 and looking downwardly of the cane with the access door in the open position.

Spare cartridges are preferably carried in the second cane 13 as shown in FIG. 8 where separate compartments are provided having snap-latched doors 13a as shown both in FIG. 8 and in FIG. 9. In operation, a door is opened and a cartridge is removed from that compartment and the door is pushed shut, the latch 13b snapping in place to hold it closed. The cartridge is then used in the first cane 12 in the manner described previously in this specification.

While there have been shown and described and pointed out the fundamental novel features of the invention as applied to a preferred embodiment, it will be understood that various omissions and substitutions and changes in the form and details of the device illustrated and in its operation may be made by those skilled in the art, without departing from the spirit of the invention. It is the intention, therefore to be limited only as indicated by the scope of the following claims.

I claim:

1. An inflatable orthosis system comprising, in combination, a cane, a gas generator in said cane, means for initiating the generation of gas by said generator, and conduit means communicably connected to the gas generator and to the inflatable orthosis to conduct the generated gas thereto.

2. The invention set forth in claim 1 with a pressure regulator valve in the conduit means and communicably connected to said gas generator.

3. The invention set forth in claim 1 with a filter in the cane and interposed between the gas generator and inflatable orthosis and through which the gas passes before entering the inflatable orthosis.

4. The invention set forth in claim 3 with a neutralizer and a dessicant in the cane and interposed between the filter and pneumatic orthosis and through which the gas passes before entering the orthosis.

5. An inflatable orthosis system comprising, in combination, a cane, a combustion chamber in said cane, solid propellant in said combustion chamber, means associated with the propellant for igniting the propellant at the will of user to create gases under pressure in said combustion chamber, and conduit means communicably connected to the combustion chamber and to an inflatable orthosis to conduct gases thereto.

6. The invention set forth in claim 5 with the combustion chamber located at the lower end of the cane and with a combustion gas conduit extended upward through a hollow enclosed portion of the cane to form a water trap therein.

7. The invention set forth in claim 5 with the ignition means including a percussion cap in the cane exposed to the solid propellant and a triggered hammer for firing said percussion cap with the triggered hammer including means for initially cocking a spring-loaded hammer directed toward the cap, a lanyard adapted to release the triggered hammer upon a pull thereof, a handle on said cane and the lanyard extended thereto and operable therefrom.

8. The invention set forth in claim 5 with the ignition means including a hot wire energized from a battery located in the cane upon closure of a switch.

9. The invention set forth in claim 8 with the cane having a foot and the battery housed in the foot.

10. The invention set forth in claim 8 with the cane having a handle and the battery housed in the handle.

11. The invention set forth in claim 8 with the cane having a handle and the ignition switch located on said handle.

12. The invention set forth in claim 5 with the combustion chamber and propellant both housed in a cartridge removable from the cane.

13. The invention set forth in claim 12 with the filter included in the cartridge.

14. The invention set forth in claim 12 with the igniter included in the cartridge.

* * * * *